(12) United States Patent
Rolli

(10) Patent No.: US 8,474,114 B2
(45) Date of Patent: Jul. 2, 2013

(54) METHOD FOR THE FINAL SHAPING OF A TAMPON

(75) Inventor: Kilian Rolli, Baden (CH)

(73) Assignee: Ruggli Projects AG, Hagendorn (CH)

( * ) Notice: Subject to any disclaimer, the term of this patent is extended or adjusted under 35 U.S.C. 154(b) by 0 days.

(21) Appl. No.: 13/381,188

(22) PCT Filed: Jun. 28, 2010

(86) PCT No.: PCT/EP2010/003842
§ 371 (c)(1),
(2), (4) Date: Feb. 7, 2012

(87) PCT Pub. No.: WO2011/000508
PCT Pub. Date: Jan. 6, 2011

(65) Prior Publication Data
US 2012/0124794 A1 May 24, 2012

(30) Foreign Application Priority Data
Jun. 29, 2009 (AT) ................. A 1009/2009

(51) Int. Cl.
*D04H 1/22* (2006.01)
*A61F 13/20* (2006.01)

(52) U.S. Cl.
USPC ........................................................ 28/118

(58) Field of Classification Search
USPC ............ 28/118, 119, 120, 116, 123, 122, 28/125, 132; 604/385.17, 385.18, 904; 264/320, 264/324, 334; 425/392, 394, 116, 117, 395, 425/396; 156/581, 583.1, 228, 62.6, 194, 156/196
See application file for complete search history.

(56) References Cited

U.S. PATENT DOCUMENTS

| | | | |
|---|---|---|---|
| 3,422,496 A | | 1/1969 | Wolff et al. |
| 4,109,354 A | * | 8/1978 | Ronc .............................. 28/119 |
| 6,889,409 B2 | * | 5/2005 | Friese et al. .................... 28/118 |
| 7,120,977 B2 | | 10/2006 | Bittner et al. |
| 7,124,483 B2 | | 10/2006 | Prosise et al. |
| 7,549,982 B2 | | 6/2009 | Carlin |
| 7,845,380 B2 | * | 12/2010 | Binner et al. ................. 156/484 |
| 8,082,639 B2 | | 12/2011 | Rolli |
| 2004/0226152 A1 | | 11/2004 | Prosise et al. |
| 2005/0113780 A1 | * | 5/2005 | Gatto et al. .............. 604/385.17 |
| 2005/0113787 A1 | | 5/2005 | Carlin |
| 2005/0113807 A1 | * | 5/2005 | Carlin .......................... 604/904 |

(Continued)

FOREIGN PATENT DOCUMENTS

| | | |
|---|---|---|
| CH | 288020 | 12/1952 |
| DE | 1 491 161 | 6/1969 |

(Continued)

OTHER PUBLICATIONS

International Search Report of PCT/EP2010/003842, date of mailing Oct. 28, 2010.

*Primary Examiner* — Amy Vanatta
(74) *Attorney, Agent, or Firm* — Collard & Roe, P.C.

(57) ABSTRACT

The invention relates to a method for a shaping step completing a process for producing a tampon (1) which is produced of an absorbent material. At least one groove (12, 13) is embossed onto the peripheral surface by radially compressing, preferably under thermal influence, at least one region of the tampon (1) extending along a peripheral surface of the tampon (1), the groove plane substantially extending normal to the longitudinal extension of the tampon.

13 Claims, 2 Drawing Sheets

U.S. PATENT DOCUMENTS

| | | | |
|---|---|---|---|
| 2008/0154222 A1* | 6/2008 | Chaffringeon | 604/361 |
| 2009/0082712 A1* | 3/2009 | Hasse et al. | 604/11 |
| 2012/0010587 A1* | 1/2012 | Smet | 604/379 |
| 2012/0089111 A1* | 4/2012 | Magnusson et al. | 604/385.18 |
| 2013/0062812 A9* | 3/2013 | Graber | 264/320 |

FOREIGN PATENT DOCUMENTS

| | | |
|---|---|---|
| DE | 18 15 541 | 7/1970 |
| DE | 93 20 358 | 9/1994 |
| DE | 21 2004 000 071 | 7/2006 |
| DE | 10 2005 037065 | 2/2007 |
| DE | 60 2004 010386 | 10/2008 |
| EP | 1 304 095 | 4/2003 |
| GB | 706915 | 4/1954 |
| WO | WO 2004/100847 | 11/2004 |
| WO | WO 2005/051268 | 6/2005 |

* cited by examiner

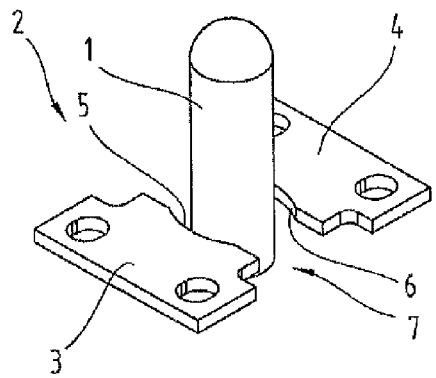
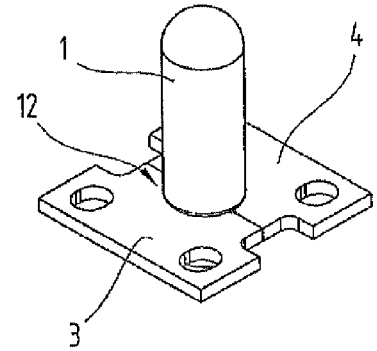
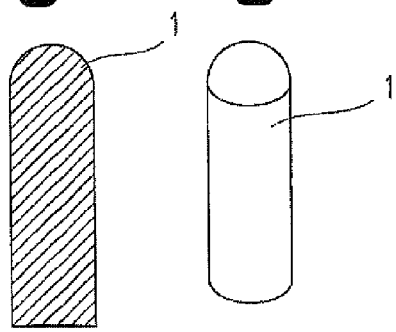
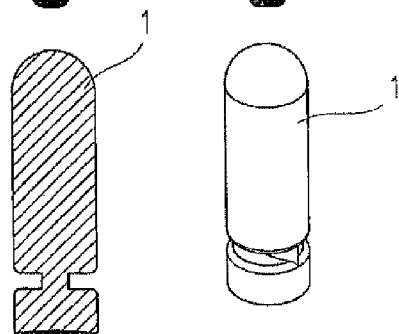
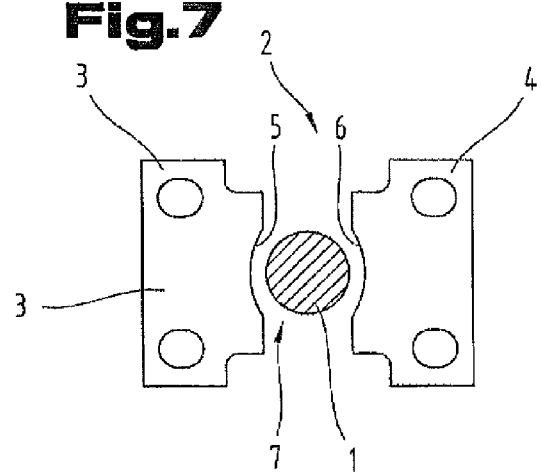
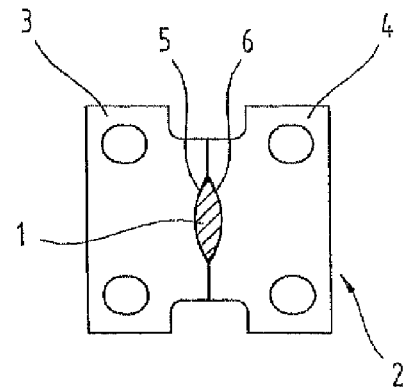

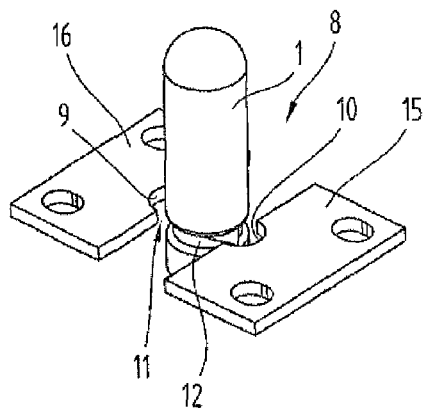
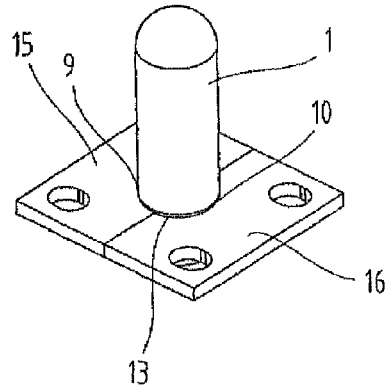
 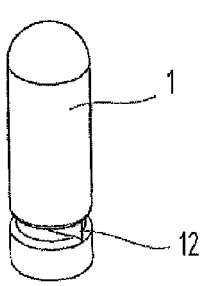 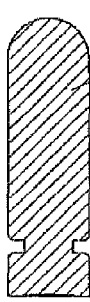 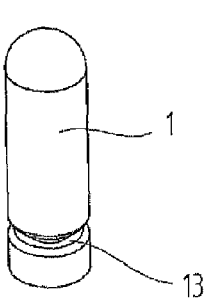
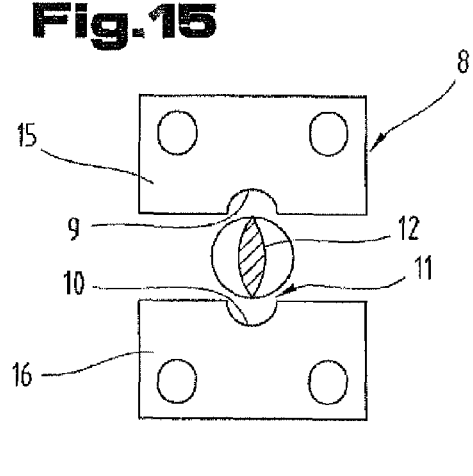
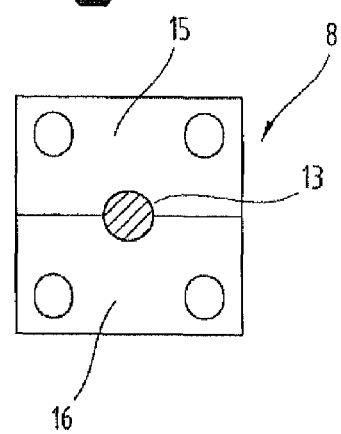

METHOD FOR THE FINAL SHAPING OF A TAMPON

CROSS REFERENCE TO RELATED APPLICATIONS

This application is the National Stage of PCT/EP2010/003842 filed on Jun. 28, 2010, which claims priority under 35 U.S.C. §118 of Austrian Application No. A 1009/2009 filed on Jun. 29, 2000, the disclosure of which is incorporated by reference. The international application under PCT article 21(2) was not published in English.

The invention relates to a method for a shaping step completing a process for producing a tampon which is produced of an absorbent material.

Furthermore, the invention relates to an apparatus for a shaping step completing a process for producing a tampon which is produced of an absorbent material.

Tampons are widely known sanitary products that can be produced of strips of absorbent cotton that are rolled and subsequently compressed in a press apparatus, due to the manufacturing process typically resulting in a circular cylindrical basic shape of the tampon. Nevertheless, it is frequently desired to produce tampons that additionally feature a special design, for example in the form of different cross-sections in various sections. Such a tampon is for example known from the DE 212004000071 U1. To avoid damages of the fiber structure of the tampon, relatively complex methods for producing such a tampon are required.

Another method for a shaping step for producing a tampon has been found in the WO 2004/100847. In this known method, a tampon pledget is put into a split cavity mold, the contour of which the finished tampon shall adapt. By application of heat it is achieved that the shape of the tampon remains stable after removal of the mold.

Thus, the objective of the invention is to produce tampons with different cross-sections without damaging the fiber structure.

Using a method in the manner described at the beginning, this objective is according to the present invention provided by at least one groove being embossed onto the peripheral surface by radially compressing, preferably under thermal influence, at least one region of the tampon extending along a peripheral surface of the tampon, the groove plane substantially extending normal to the longitudinal extension of the tampon.

Due to a possible heating of the tampon before or during the compression, a stable or durable reshaping of the tampon can be facilitated in an easy manner. The term "final shaping" in this document refers to the final process of shaping of the production process. The method according to the present invention can be added subsequently after a usual production process that is used to produce a tampon. Because the basic product of the method according to the present invention advantageously can be a tampon, already "finished" using a usual production method, the method according to the present invention can be easily combined with any production method for tampons and can be integrated into production processes already existing.

The term "groove plane" in this document refers to a plane where a two-dimensional curve extending along the longitudinal direction of the groove and describing the shape of the periphery of the groove is situated. This curve may be a circle, an ellipsis or may have a polygonal or any other shape.

In this case, according to the present invention it is provided that a peripheral surface of the tampon is sectional spanned by at least one first press mold with pressing sections that are moveable in opposite directions and concavely embodied each. In their course, said pressing section are curved less than the peripheral surface of the tampon and they are arranged in such a way that a pressing of the tampon by means of the pressing sections results in a convex surface shape of a pressed region of the tampon, and that said peripheral surface is compressed by means of a movement of the pressing sections towards each other. After removal of the pressing sections, a compressed region essentially provides a contour corresponding to the course of the contour of the pressing sections.

The advantage of this approach is that the space bordered by the pressing sections, when the press mold is in a closed state, has a larger length and smaller width than a diameter of a tampon to be compressed before its compression. In the manner just described, a compression of the tampon can easily be effected and the appropriate choice of the radiuses of curvature of the pressing sections or the appropriate curvature of the pressing sections ensures that the surface will not be damaged or no fibers of the tampon will be cut through.

According to an advantageous development of the invention it is provided that a section of the tampon previously having been compressed by means of the first press mold is spanned and reshaped by means of at least a second press mold with pressing sections that are moveable in opposite directions and concavely embodied each, that are arranged in such a way that a pressing of the tampon by means of the pressing sections results in a convex surface shape of the compressed section of the tampon and the pressing sections of the second press mold are curved more than the pressing sections of the first press mold previously used, but curved less than previously compressed sections of the tampon facing them. Due to the sequential pressing of the tampon with press molds providing different curvatures or sizes, the desired final shape can be achieved in an easy manner. By means of the first compression and reshaping, the tampon can be brought into a shape that can be machined using a second, smaller press mold without damaging the surface of the tampon or its fibers.

Circumferential compressions of any course can be produced by embossing a groove extending in accordance with the first curve shape onto the peripheral surface of the tampon by compressing the tampon using the first press mold, and embossing a groove extending in accordance with the second curve shape by compressing the tampon using the second press mold. In this connection, it has turned out to be advantageous that the groove extending in accordance with the first curve shape and/or the groove extending according to the second curve shape is/are closed loop in circumferential direction of the peripheral surface.

In order to produce a circular compression with a smaller diameter than the diameter of the tampon, in a first step using the press mold a first groove extending oval in circumferential direction around the peripheral surface can be embossed, whereby in a further step the oval extending groove is reshaped to be an essentially circular extending groove by pressing with the further press mold.

A preferred variant of the invention is that the tampon is compressed and reshaped when it is already wrapped in a protective cover. Due to this embodiment of the invention, problems arising from the packaging of a complex shaped tampon are easily avoided because the shaping is effected after the packaging of the tampon.

The above mentioned objective can also be provided by using an apparatus mentioned at the beginning, which, according to the present invention, is embodied to compress at least partially in radial direction, preferably under thermal influence, by application of pressure at least one region of the tampon extending along a peripheral surface of the tampon and thus to emboss a groove with a groove plane essentially extending normal to the longitudinal axis of the tampon onto the peripheral surface.

According to the preferred embodiment of the invention, the apparatus comprises at least one press mold with pressing sections that are moveable in opposite directions and concavely embodied each, and the pressing sections, when press mold is in a closed state, border a compression space and are arranged in such a way that a pressing of the tampon by means of the pressing sections results in a convex surface shape of the pressed region of the tampon.

The direction of insertion of the tampon into the press mold can essentially run parallel to a press plane, whereby each pressing section can be shaped according to the required shaping of the region to be compressed.

In order to insert the necessary temperature during the process of reshaping into the tampon, at least one press mold can be heatable. Alternatively, also the tampon itself could be preheated.

According to a variant of the invention, inter alia being distinguished by a simple assembly, the press mold can provide at least two plate-shaped compression jaws, whereby individual sections of the edge sections of the compression jaws facing each other are designed to be pressing sections.

Furthermore, the apparatus can feature at least two press molds with each of which can be embodied as described above and the pressing sections of the second press mold are curved more than the pressing sections of the first press mold. Using an apparatus such embodied, compressions providing smaller diameters than the diameter of the tampon can be produced in a simple manner, because due to the pre-pressing of the tampon by means of the first press mold, the radius of the region to be compressed can be decreased so that the tampon fits into the second smaller press mold. The method could be continued as long as one likes as long as it does not result in a damaging of the tampon.

The invention providing further advantages will be explained in more detail below by means of a non-restricting exemplary embodiment shown in the drawings. These schematically show:

FIG. 1 a press mold of an apparatus according to the invention with open compression jaws and a tampon positioned between the latters;

FIG. 2 the press mold of FIG. 1 with closed compression jaws;

FIG. 3 a perspective view of a tampon before a reshaping process with the press mold of FIG. 1 and FIG. 2;

FIG. 4 a longitudinal cross-sectional view of the tampon of FIG. 3;

FIG. 5 a perspective view of the tampon of FIG. 3 after the reshaping process by pressing with the press apparatus of FIGS. 1 and 2;

FIG. 6 a longitudinal cross-sectional view of the tampon of 5;

FIG. 7 a plan view of a partial cross-sectional view of the embodiment of FIG. 1;

FIG. 8 a plan view of a partial cross-sectional view of the embodiment of FIG. 2;

FIG. 9 a perspective view of another press mold of the apparatus according to the present invention with open compression jaws, with the pressing sections of the compressions jaws having a smaller radius of curvature than the pressing sections of the compression jaws of the press mold shown in FIGS. 1, 2, 7 and 8;

FIG. 10 the press mold of FIG. 9 with closed compression jaws;

FIG. 11 a perspective view of a tampon before the pressing with the press mold of FIGS. 9 and 10;

FIG. 12 a longitudinal cross-sectional view of the tampon of FIG. 11;

FIG. 13 a perspective view of the tampon of FIG. 11 after the pressing with the press apparatus of FIGS. 9 and 10;

FIG. 14 a longitudinal cross-sectional view of the tampon of FIG. 13;

FIG. 15 a plan view of a partial cross-sectional view of the embodiment of FIG. 9 and FIG. 16 a plan view of a partial cross-sectional view of the embodiment of FIG. 10.

First of all, it should be pointed out that in the variously described exemplary embodiments the same parts are given the same reference numerals and the same component names, whereby the disclosures contained throughout the entire description can be applied to the same parts with the same reference numerals and the same component names. Also details relating to position used in the description, such as e.g. top, bottom, side etc. relate to the currently described and represented figure and in case of a change in position should be adjusted to the new position. Furthermore, also individual features or combinations of features from the various exemplary embodiments shown and described can represent in themselves independent or inventive solutions or solutions according to the invention.

FIG. 1 shows an apparatus according to the present invention. The apparatus is arranged to compress a generally cylindrical tampon in radial direction at least sectional under thermal influence by pressure. As used herein "generally cylindrical" refers to usual shape of a tampon as well-known from prior art, but furthermore also encompasses flattened or partially flattened cylinders, curved cylinders and shapes providing different regions of cross-sections.

According to FIG. 1, the apparatus according to the present invention for reshaping a tampon 1 can feature a first press mold 2 with compression jaws 3 and 4 being moveable in opposite directions. The compression jaws 3 and 4 provide concave pressing sections 5 and 6, which are, related to a geometric center axis of a compression space 7 that is situated between the pressing sections 5 and 6, extending normal to a direction of motion or to each other, arranged in such a way that by pressing of a surface section of the tampon 1 by means of the pressing sections 5 and 6, a convex form of the pressed surface section is achieved. In a compressed state, the compression space 7 is filled by the section of the tampon 1 positioned in it.

In order to enable a pressing of the tampon 1 without the absorbent cotton spilling out into a motion plane of the pressing sections 5 and 6 and thus to avoid damaging the surface of the tampon 1, the pressing sections 5 and 6 are less curved than the peripheral surface of the tampon 1. By means of moving the pressing sections 5 and 6 towards each other, the tampon 1 can be compressed in the region spanned by the compression jaws 3 and 4, whereby a compressed region essentially has a contour corresponding to the course of the contours of the pressing sections 5 and 6 after removing the pressing sections 5 and 6. Every pressing section 5 and 6 is thus shaped according to the desired shaping of the region of the tampon 1 to be compressed. As FIG. 1 furthermore shows, the compression jaws 3 and 4 can be embodied plate-shaped, with edge sections of the compression jaws 3 and 4 facing each other being designed to be pressing sections 5 and 6. Alternatively to the application of only two compression jaws 3 and 4, several compression jaws preferably being arranged radially around the compression space 7, can be provided.

The direction of insertion of the tampon 1 into the press mold 2 or the compression space 7 is essentially parallel to the geometrical center axis of the compression space 7 that means parallel to the press plane. The compression jaws 3 and 4 can be mounted to sliding carriages, not shown herein, that can move towards and away from each other, in order to allow an opening and pressing. For inserting the tampon there can be provided a sleeve-shaped feeding, also not shown, of the tampon.

Furthermore, the press mold 2 can be heatable, for example by means of heating cartridges inserted into holes or recesses of the compression jaws 3 and 4.

In order to compress the sections of the peripheral surface of the tampon 1, the compression jaws 3 and 4 can be brought from the position shown in FIG. 1 into the position shown in FIG. 2. According to the present invention, the tampon 1 is in this case spanned by the pressing sections 5 and 6 and the material of the tampon 1 in the region spanned is compressed, preferably under thermal influence, by means of the movement of the pressing sections 5 and 6 towards each other. The compression of the tampon 1 by means of the compression jaws 3 and 4 is preferably effected essentially normal to the longitudinal axis of the tampon 1 essentially extending parallel to the press plane. The term longitudinal axis herein refers to the longest linear dimension of the tampon 1. The term cross-section refers to a disc that is taken perpendicular from the longitudinal axis. After compressing, the spanned and reshaped region of the tampon 1 has a contour according to the pressing sections 5 and 6 and a smaller diameter than the regions adjacent to this region of the tampon 1.

According to FIGS. 3 and 4, before the process of reshaping, the tampon 1 being produced of an absorbent material can feature a peripheral surface essentially according to a circular cylinder. It is especially advantageous if the tampon 1 has already been packaged into a protective cover before the process of reshaping.

As it can be taken from FIGS. 5 and 6, after the pressing being preferably carried out under thermal influence, the tampon 1 is reshaped in the area compressed and there features a smaller cross-sectional diameter than adjacent regions of the tampon 1.

As it can be taken from FIGS. 7 and 8, the space bordered by the pressing sections in a closed state of the press mold 2 can have a larger length and smaller width than the diameter of the tampon 1 to be compressed before its compression.

As it can be taken from FIG. 9, the apparatus can provide another press mold 8 with pressing sections 9 and 10 that are moveable in opposite directions in one plane. The pressing sections 9 and 10 of the additional press mold 8 can be arranged as in the press mold 2 shown in FIGS. 1, 2, 7 and 8 and described above, related to a geometric center axis of a compression space 11 that is situated between the pressing sections 9 and 10, extends normal to a direction of motion or to each other, that by pressing of a surface section of the tampon 1 a convex form of the pressed surface section is achieved.

Preferably, the pressing sections of the first press mold 2 are less curved than the pressing sections 9 and 10 of the second press mold 8. In this case, the sections of the previously compressed tampon 1 facing the second press mold 8 are curved more than the pressing sections 5, 6 of the first press mold 2. In this way it can be guaranteed that the pressing does not result in a spilling of the absorbent cotton into one of the motion plane of the press sections 9 and 10.

The second press mold 8 can be heatable like the first one. At this point it should be noted that the press molds 2 and 8 only differ with respect to the shape or curvature their pressing sections 5 and 6 or 9 and 10. The second press mold 8 can also provide plate-shaped compression jaws 15 and 16, with the edge sections being made of the pressing sections 9 and 10.

According to the method according to the invention, a region of the tampon 1 previously having been compressed by means of the first press mold 2 is reshaped by means of the second press mold 8, preferably under thermal influence, that means by the possible application of heat. Alternatively to an application of heat into the tampon 1 by heatable press molds 2 or 8, the tampon 1 itself could be pre-heated. Depending on the production speed a temperature of about 15° C. to 180° C. has turned out to be advantageous for viscose fibers as the material the tampons are made mainly of. The second press mold 8 can be heatable, too, whereby the compression step carried out with the second press mold 8 can preferably be made using the same temperature as it was used for the first compression step. The second compression step can also be carried out using a lower or higher temperature than it was used for the compression step carried out with the first press mold 2.

At this point, it should, however, be expressly noted that the method according to the present invention can also be carried out without thermal influence that means without heating the tampon 1 or the press molds 2 or 8. A compression of the tampon 1 under the effect of heat only represents a preferable variant of the invention.

By compressing the tampon 1 using the first press mold 2, a groove 12 extending according to a first curve shape may be embossed onto the peripheral surface of the tampon 1. Hereupon, another groove 13 extending according to a second curve shape can be embossed by compressing the tampon 1 with the second press mold 8. The curve shapes of the grooves 12 and 13 can be closed loops.

As shown in the FIGS. 1 to 8, a first groove 12 extending oval in circumferential direction around the peripheral surface can be embossed in one first step with the press mold 2. According to the embodiments in the FIGS. 9 to 16, the oval extending groove 12 can be reshaped to be an essentially circular extending groove 13 by pressing with another press mold 8. Needless to say that the objective according to the present invention is not limited to oval and circular extending grooves, but any circumferential shapes of grooves 12 and 13 are possible. It is in this case only important that the tampon 1 after being reshaped with the first press mold 2 is compressed in the reshaped region in such a way that it can be spanned by the second press mold 8 without the tampon 1 being penetrated.

Furthermore, the invention is not limited to a compression by means of the press molds 2 and 8 shown, since the groove 13 can also be produced by means of one or several rolls for example.

The above described exemplary embodiments refer to possible variants of embodiment of an apparatus according to the inventions or a method according to the invention and are not intended to limit the scope of the invention to these illustrated variants of embodiments provided herein but that there are also various combinations among the variants of the embodiments themselves and variations regarding the present invention should be executed by a person skilled in the art. All and every imaginable variants of the embodiment, arising from combining single details of the variant of embodiment illustrated and described are subject to scope of protection.

The invention claimed is:

1. Method for a shaping step completing a process for producing a tampon (1) which is produced of an absorbent material, wherein at least one groove (12, 13) is embossed onto the peripheral surface by radially compressing at least one region of the tampon (1) extending along a peripheral surface of the tampon (1), the groove plane substantially extending normal to the longitudinal extension of the tampon, wherein a peripheral surface of the tampon (1) is sectional spanned by at least one first press mold (2) with pressing sections (5, 6) that are moveable in opposite directions, concavely embodied each and in their course less curved than the peripheral surface of the tampon, with said pressing sections being arranged such a way that a pressing of the tampon (1) by means of the pressing sections (5, 6) results in a convex surface shape of a pressed region of the tampon (1), and wherein said peripheral surface is compressed by means of a movement of the pressing sections (5, 6) towards each other, whereby a compressed region after removal of the pressing sections essentially provides a contour corresponding to the course of the contour of the pressing sections (5, 6).

2. Method according to claim 1, wherein the space bordered by the pressing sections (5, 6) in a closed state of the press mold (2) has a larger length and smaller width than a diameter of a tampon (1) to be compressed before its compression.

3. Method according to claim 1, wherein a region of the tampon (1) previously having been compressed by means of the first press mold (2) is spanned and reshaped by means of at least a second press mold (8) with pressing sections (9, 10) that are moveable in opposite directions and concavely embodied each, and that are arranged in such a way that a pressing of the tampon (1) by means of the pressing sections results in a convex surface shape of the compressed section of the tampon, whereby the pressing sections (9, 10) of the second press mold (8) are curved more than the pressing sections (5, 6) of the first press mold (2) previously used, but curved less than previously compressed sections of the tampon (1) facing them.

4. Method according to claim 3, wherein by compressing the tampon (1) using the first press mold (2) a groove (12) extending according to a first curve shape is embossed onto the peripheral surface of the tampon (1) and by compressing the tampon (1) using the second press mold (8) a groove (13) extending according to a second curve shape is embossed.

5. Method according to claim 4, wherein the groove (12) extending in accordance with the first curve shape and/or the groove (13) extending in accordance with the second curve shape is/are closed loop in circumferential direction of the peripheral surface.

6. Method according to claim 5, wherein in a first step using the first press mold (2) a first groove (12) extending oval in circumferential direction around the peripheral surface is embossed, whereby in a further step the extending groove 12 is shaped to be an essentially circular extending (13) groove by pressing with the second press mold.

7. Method according to claim 1, wherein the tampon (1) is already wrapped in a protective cover when it is compressed and reshaped.

8. Apparatus for a shaping step completing a process for producing a tampon (1) which is produced of an absorbent material, wherein the apparatus is set up to compress at least partially in radial direction by application of pressure at least one region of the tampon (1) extending along a peripheral surface of the tampon (1) and to emboss a groove (12, 13) with a groove plane substantially extending normal to the longitudinal axis of the tampon (1), wherein the apparatus comprises at least one press mold (2) with pressing sections (5, 6) that are essentially moveable in opposite directions and concavely embodied each, whereby the pressing sections (5, 6) in a closed state of the press mold (2) border a compression space and are arranged in such a way that a pressing of the tampon (1) by means of the pressing sections (5, 6) results in a convex surface shape of the pressed region of the tampon (1).

9. Apparatus according to claim 8, wherein the insertion direction of the tampon (1) into the press mold (2) is essentially parallel to the press plane.

10. Apparatus according to claim 8, wherein each pressing section (5, 6, 9, 10) is shaped according to the shaping to be obtained of the region to be compressed.

11. Apparatus according to claim 8, wherein at least one press mold (2, 8) is heatable.

12. Apparatus according to claim 8, wherein at least one press mold (2, 8) features at least two plate-shaped compression jaws (3, 4, 15, 16), whereby sections of the edge sections of the compression jaws (3, 4, 15, 16) facing each other are designed to be pressing sections (5, 6, 9, 10).

13. Apparatus according to claim 8, wherein it comprises at least two press molds (2, 8) that are each embodied according to claim 8 and the pressing sections (9, 10) of the second press mold (8) are curved more than the pressing sections (5, 6) of the first press mold (2).

* * * * *

UNITED STATES PATENT AND TRADEMARK OFFICE
CERTIFICATE OF CORRECTION

PATENT NO. : 8,474,114 B2  Page 1 of 1
APPLICATION NO. : 13/381188
DATED : July 2, 2013
INVENTOR(S) : Kilian Rolli It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 25 days.

Signed and Sealed this
Eighth Day of September, 2015

Michelle K. Lee
*Director of the United States Patent and Trademark Office*